US00PP07907P

United States Patent [19]

Twomey

[11] Patent Number: Plant 7,907

[45] Date of Patent: Jul. 14, 1992

[54] ROSE PLANT NAMED TWOWIN

[75] Inventor: Jerry Twomey, Leucadid, Calif.

[73] Assignee: DeVor Nurseries, Inc., Watsonville, Calif.

[21] Appl. No.: 611,511

[22] Filed: Nov. 13, 1990

[51] Int. Cl.[5] ..... A01H 5/00
[52] U.S. Cl. ..... Plt./11
[58] Field of Search ..... Plt./11, 12, 13, 16

*Primary Examiner*—Howard J. Locker

*Attorney, Agent, or Firm*—Charles W. Rummler

[57] ABSTRACT

A new and distinct greenhouse and garden rose plant particularly distinguished by its continuous and profuse production of large flowers having in general an Orange Red coloration lasting from early Spring to late Fall for greenhouse and garden cultures with flowers born on strong, vigorous, upright stems of substantial length on a plant having a vigorous and sturdy growth habit with abundant foliage.

1 Drawing Sheet

BACKGROUND OF THE NEW PLANT

This new variety of rose plant originated as a hybrid seedling produced by me at my Carlsbad, Calif., nursery said hybrid seedling resulted from a crossing of the variety 'Gingersnap' (U.S. Plant Pat. No. 4,330) with pollen from the variety 'Marina' (U.S. Plant Pat. No. 3,789) with the object of developing a variety having good health, vigor and good production of a flower having a more intense Orange and Yellow color. The present seedling was selected for propagation because of the brilliant Orange Red coloration of its flowers born on long, strong stems of a plant having a sturdy and vigorous as well as tall growth habit and propagation was done by me by cuttings as well as by budding in a nursery environment at Pleasanton, Calif. with such success that such propagation was carried on through several successive generations which demonstrated that the novel characteristics of the selected seedling would hold true from generation to generation and appeared to be firmly fixed so that for commercial propagation, its homogeniety could be assured.

DESCRIPTION OF THE DRAWING

My new rose plant is illustrated by the accompanying full color photographic drawing which shows the flower in several stages of maturity which demonstrates the flower form and the nature and color of its petals, the color shown being as nearly true to that herein specified as is reasonably possible to obtain by conventional photographic procedures.

DESCRIPTION OF THE NEW VARIETY

The following is a detailed description of my new rose plant based upon observation of plants grown in greenhouse and nursery environments at Pleasanton, Calif., the color designations being according to The R.H.S. Color Chart published by The Royal Horticultural Society of London, England.

THE PLANT

Origin: Seedling.
Parentage:
*Seed parent.*—The variety 'Gingersnap' (U.S. Plant Pat. No. 4,330).

*Pollen parent.*—The variety 'Marina' (U.S. Plant Pat. No. 3,789).
Classification:
*Botanic.*—Rosa-Hybrid.
*Commercial.*—Garden Rose.
Form: Vigorous and upright bush.
Height: About 150 cm.
Main stem length: Approximately 60 cm. from the last flower cut.
Branching character: Free branching.
Strength: Very sturdy.
Foliage:
*Quantity.*—Very abundant.
*Number of leaves.*—6 or 7 from the last flower cut.
*Shape.*—Odd pinnate.
*Size.*—About 147 mm. long.
*Leaflets.*—Number: 3 to 7. Shape: Ovate with denticulate margin. Size: About 69 mm. by 45 mm., in average. Texture: Slightly leathery. Aspect: Smooth and very glossy. Color: Upper side — Yellow Green 147-A. Under side — Yellow Green 147-B.
*Stipules.*—Adnate and tipped with glands.
*Rachis.*—Length: About 91 mm. on 3 part leaf and 142 mm. on 5 part leaf.
*Petioles.*—Length: About 17 mm. on 3 part leaf and about 18 mm. on 5 part leaf.
Ribs and veins: Very slightly depressed on top side and rounded on under side.
Thorns: Vary in size and about 7 mm., in average.
*Color.*—Greyed Red 181-A.

THE BUD

Size: Medium.
*Diameter.*—About 21 mm.
*Length.*—About 32 mm.
Shape: Globular and high centered.
Rate of opening: Moderate.
Color of petals:
*When sepals first divide.*—Orange Red 33-B on margin and with Yellow Orange 17-A on the body of the petal.
*When petals begin to unfurl.*—Orange Red 33-A at the margin, Orange Red 32-A on upper portion with Yellow 13-A for the balance.
Sepals:
*Number.*—5 or 6.

*Shape.*—Spreading with small leaves protruding.

*Character.*—Hooded over the bud and standing up as the flowers open.

*Color.*—Inside — Yellow Green 148-B. Outside -Yellow Green 146-B.

Calyx:

*Shape.*—Funnel-shaped.

*Size.*—Large, about 8 mm. wide and about 8 mm. long.

*Splitting.*—Calyx does not split.

*Aspect.*—Smooth.

Peduncle of flower stem:

*Length.*—About 63 to 70 mm.

*Appearance.*—Hairy with small spines along the stem.

*Character.*—Erect and slender.

*Color.*—Greyed Red 178-A with Yellow Green 145-A striping down one side of most stems.

THE FLOWER

Blooming habit: Continuous and profusely from early Spring through Midseason into Fall, blooming freely under natural conditions.

Size of bloom: Large.

*Diameter.*—About 97 to 100 mm.

*Depth.*—About 53 mm.

Borne: Singly.

Shape:

*When bloom first opens.*—Slightly cup shaped.

*When bloom matures.*—The petals are imbricated with some informal petals in the center.

Petalage:

*Number.*—53 to 56.

*Arrangement.*—Imbricated.

*Form.*—Spoon shaped with margins curled back and notched apex slightly lobed.

*Texture.*—Slightly leathery and soft.

*Aspect.*—Velvety.

*Color.*—Outer petals — Capsicum Red 33-A on uppermost margin with Indian Orange 32-A for the lateral margins. Center portion 12-B to 13-A. Reverse side — Orange Red 34-B at the margins with the body of Burnt Orange 31-B becoming Yellow 12-B at the central portion of the body.

Inside petals — Persimmon Orange 28-A with Yellow Orange 14-A at the base. Reverse side — Tangerine Orange 24-B.

*Petaloids.*—Number: 9 or 10. Size: 15 mm. long. Color: Indian Orange 32-A with Yellow 14-A at the base.

Discoloration after full bloom: Some discoloration does occur.

Persistence: The flower petals do hang on and dry.

Disease resistance: Moderately resistant to mildew, rust and black spots as observed at Watsonville, Calif.

Fragrance: Medium musk.

Lasting quality: Long lasting on the plant and moderate lasting as a cut flower.

THE REPRODUCTIVE ORGANS

Stamens:

*Number.*—106 to 111.

*Arrangement.*—Antrorse.

*Anthers.*—Size: 3 mm. Color: Yellow Orange 15-B.

*Filaments.*—Length: 5½ mm. Color: Yellow 7-A.

*Pollen.*—Color: Yellow Orange 15-B.

Pistils:

*Number.*—78 to 80.

*Styles.*—Length: About 11½ to 15 mm. Color: Green Yellow 1-D.

*Stigmas.*—Color: Green Yellow 1-B.

Character of the ovaries: Small, oblong with rounded ends and sparsely covered with silvery hairs.

THE FRUIT

Fertility: The fruit is fertile.

The present seedling is a bright, prolific bloomer with glossy, waxy foliage and a vigorous growth.

I claim:

1. The new and distinct rose variety substantially as herein shown and described, and particularly characterized by its profuse and continuous production of very large flowers having a strong Orange Red coloration born on long, strong, upright stems of a very tall plant having a sturdy and vigorous growth habit.

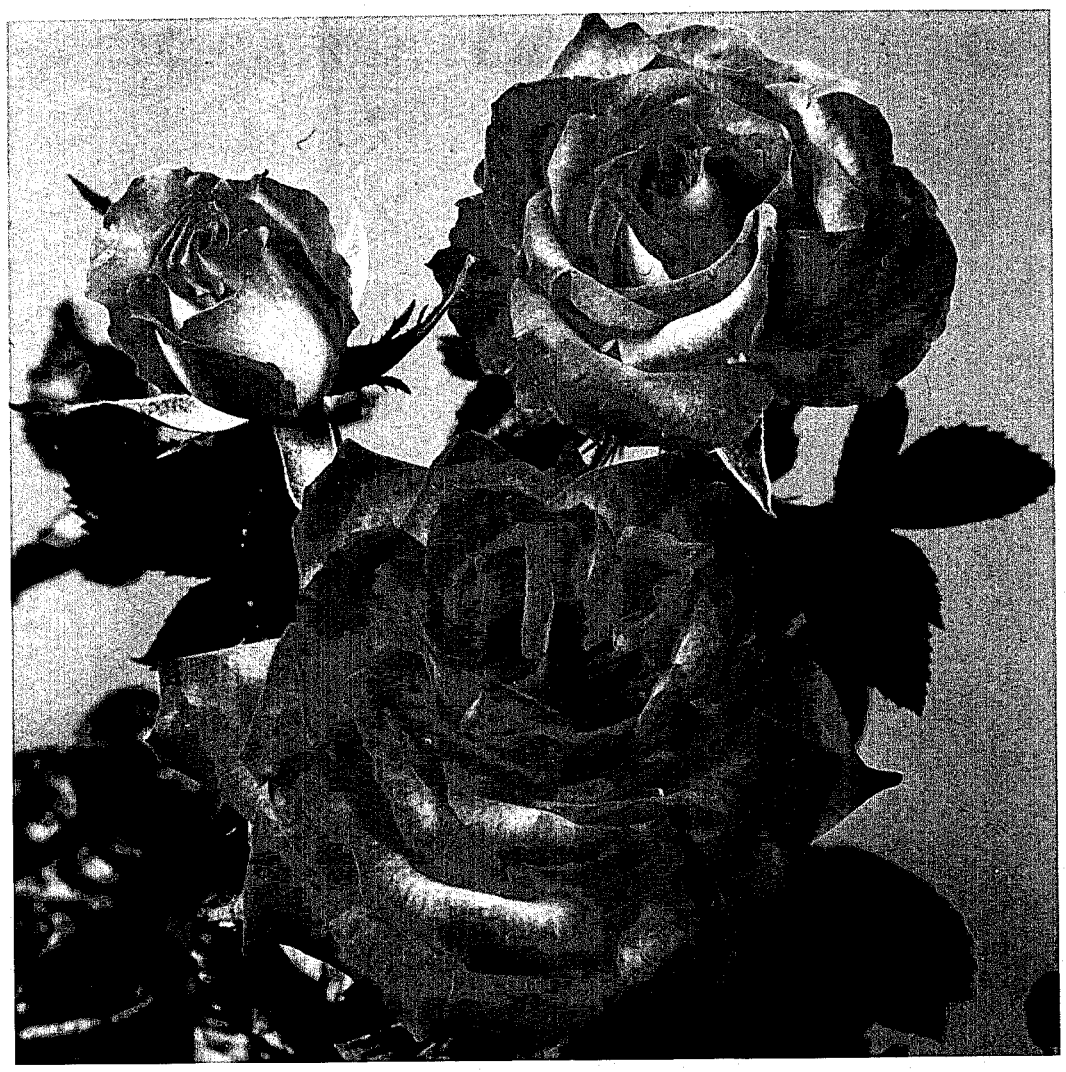

* * * * *